(12) United States Patent
Goodall et al.

(10) Patent No.: US 8,090,592 B1
(45) Date of Patent: Jan. 3, 2012

(54) METHOD AND APPARATUS FOR MULTI-DOMAIN ANOMALY PATTERN DEFINITION AND DETECTION

(75) Inventors: Colin Goodall, Rumson, NJ (US); Guy Jacobson, Bridgewater, NJ (US); Greg B. Kinne, Middletown, VA (US); Arnold Lent, Morganville, NJ (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 763 days.

(21) Appl. No.: 11/931,789

(22) Filed: Oct. 31, 2007

(51) Int. Cl.
*G06Q 50/00* (2006.01)
(52) U.S. Cl. .......................................................... 705/2
(58) Field of Classification Search .................. 378/165; 364/514 R; 435/4; 600/549; 702/187; 705/2
See application file for complete search history.

(56) References Cited

U.S. PATENT DOCUMENTS

| | | | | |
|---|---|---|---|---|
| 5,555,191 | A * | 9/1996 | Hripcsak | 709/224 |
| 2002/0186818 | A1 * | 12/2002 | Arnaud et al. | 378/165 |
| 2002/0193967 | A1 * | 12/2002 | Siegel | 702/187 |
| 2003/0129578 | A1 * | 7/2003 | Mault | 435/4 |
| 2003/0163351 | A1 * | 8/2003 | Brown et al. | 705/2 |
| 2004/0116821 | A1 * | 6/2004 | Beiswenger et al. | 600/549 |

OTHER PUBLICATIONS

"Accessible Alerting Algorithms for Biosurveilance"; Burkom, H. S.; Sep. 12, 2005.*
"Bio-ALIRT Biosurveillance Detection Algorithm Evaluation"; Seigrist et al.; Morbidity and Mortality Weekly Report; Sep. 24, 2004.*

* cited by examiner

*Primary Examiner* — Gerald J O'Connor
*Assistant Examiner* — John Pauls

(57) ABSTRACT

Disclosed herein is a multi-domain anomaly pattern definition and detection module. The module receives raw data from different kinds of anomalies from a variety of detection algorithms and generates scores associated with the data. If one or more scores exceed a threshold, then the algorithm gathers further information which may include counts or listings of detailed data for a geographic region which may include such information as emergency department and lab department data related to a particular health concern such as a respiratory syndrome. Summaries are provided which may identify anomalies and numbers of events according to geographic region and utilizing probability algorithms. Other databases such as animal data collected under the Department of Agriculture may also be utilized. The data is presented in a familiar form such as a map or a table such that a subject matter expert may determine whether to further investigate an anomaly as a potential risk, for example, a health risk.

7 Claims, 17 Drawing Sheets

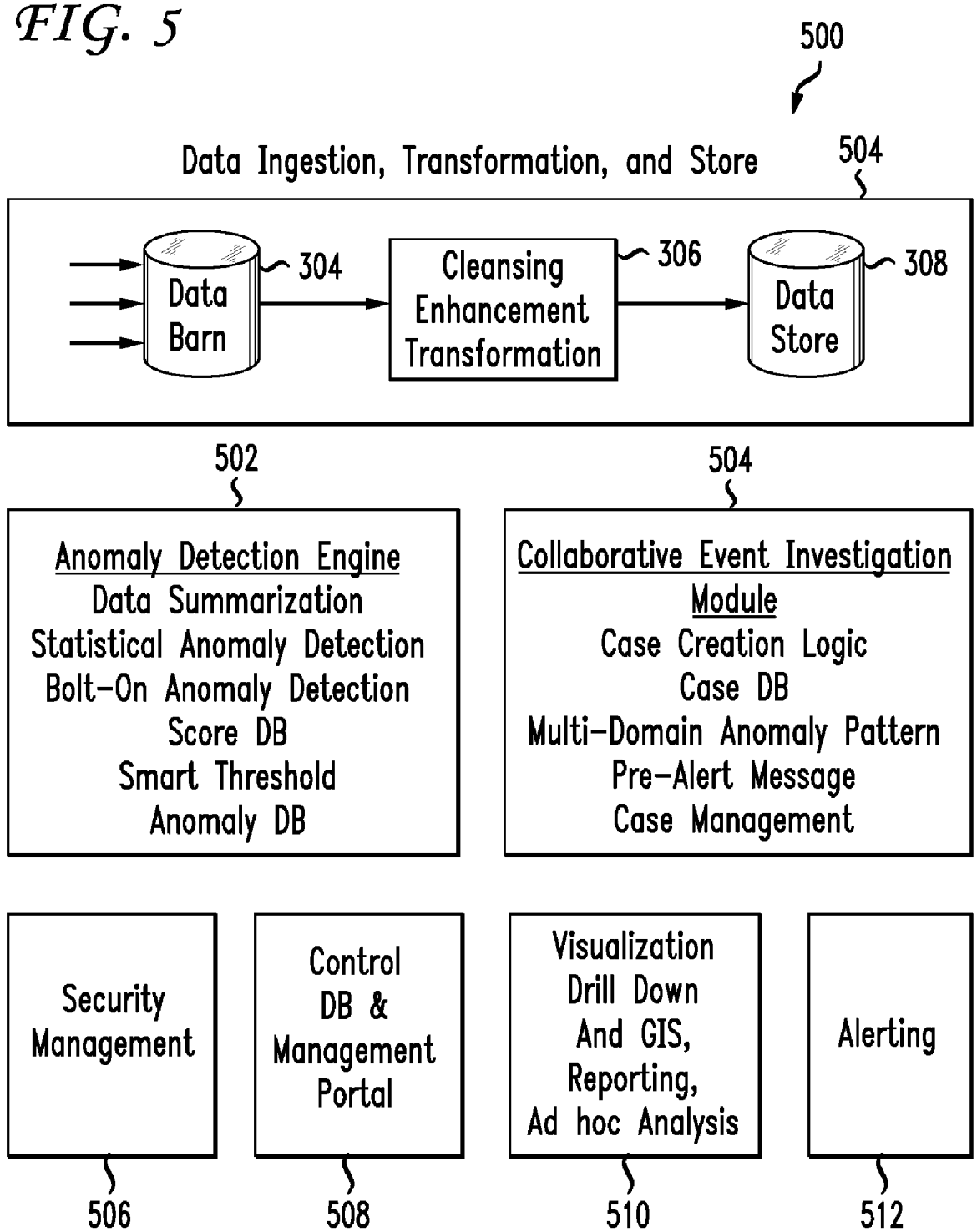

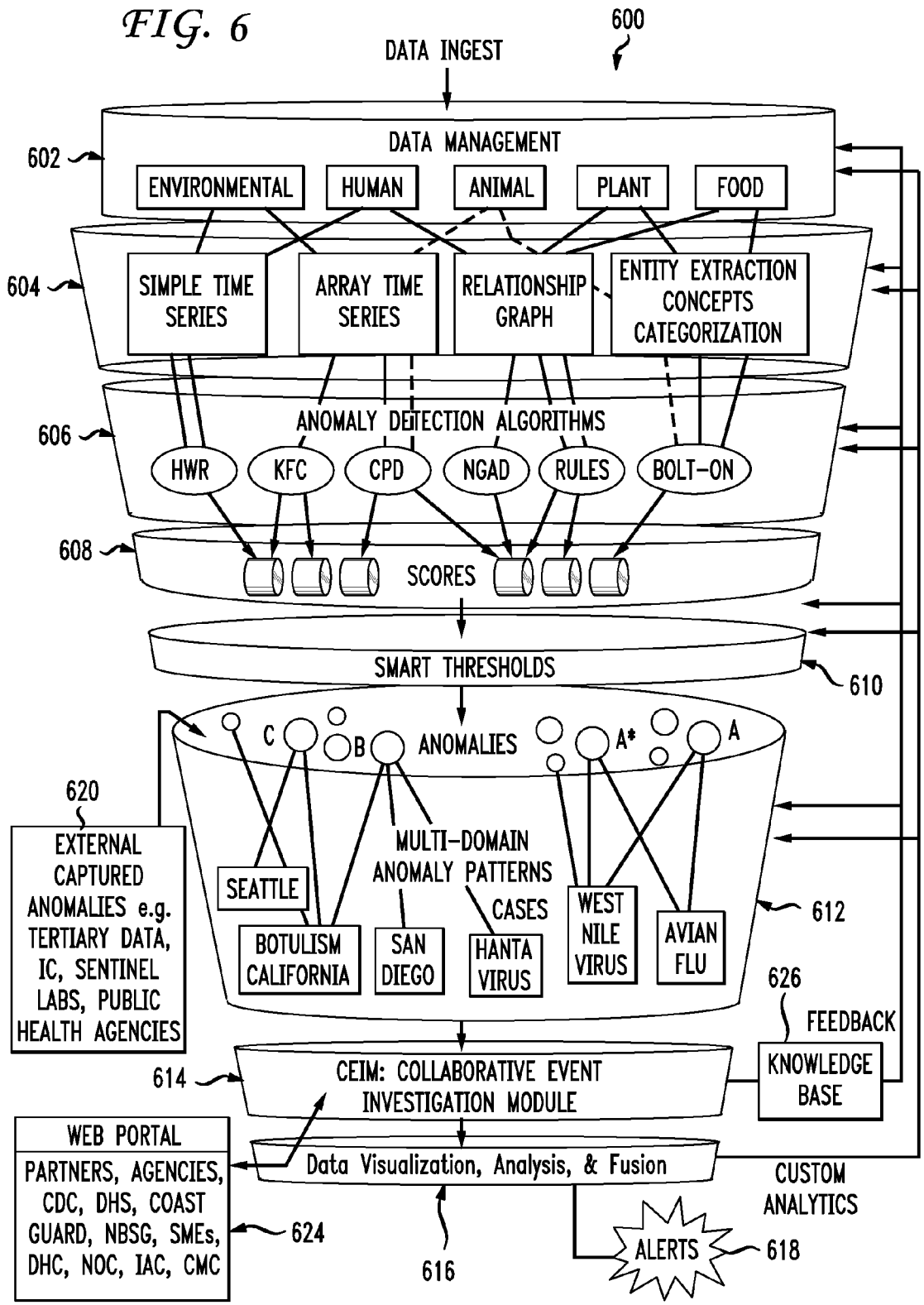

FIG. 7

INTEROPERATIVE MODULES FOR EARLY EVENT DETECTION — 700

| FUNCTION | TECHNOLOGY MODULE | MODULE DESCRIPTION | INTER-OPERABILITY |
|---|---|---|---|
| Database & Knowledge Base | Oracle; Daytona Teradata | Partitioned fully-indexed database with query languages | ODBC, JDBC, Perl-DBI, flat files, SQL, Cymbal |
| ETL, Data Ingestion | PADS, XQuery | Flexible data ingestion; XML data store query | XML |
| Monitoring & Control | OLAP Data Mining; PRISMS, RAPTOR | Standardized report generation; authorized users set parameters | Data in any database application, parameters in standard hash format |
| Statistical Anomaly Detection | HWR, KFC | Single streams; Array stream: multivariate & spatial | Implemented in C/C++, R, and SAS |
| Text Mining Tools | CPD change point detection | Detect anomalies & associations in text stream | Implemented in C/C++ |
| Classifiers | nGrams, logistic regression, etc | Predict unobserved or later observed variables | Cymbal, R, SAS, shell languages, etc. |
| Incident Management | CEIM Case Manager | Configurable browser-based case manager; Java web-based applications with auto update and centralized deployment; collaboration environment | Anomalies and cases in standard formats in any database application |
| Data Visualization | Yoix Scout Data Visualizer; VMDS | | Data in in any database application |
| Alert Network | CHAIN™/EMN℠ | System for alert notification | SQLServer™ DB for contact lists; all media |

FIG. 8

SAMPLE EVENTS IN ED VISIT DATA (Emergency Medical Associates of New Jersey) — 800

| EVENT | WHEN | WHAT | HOW DETECTED | FEATURES | INCIDENT MGMNT |
|---|---|---|---|---|---|
| Meningitis Exposure | Jul 17–19, 2004 | ED visits for meningitis exposure | Change point detection in chief complaint; KFC (7/18) | Livingston NJ; campers and parents | Single death due to bacterial meningitis in 5-year old day camper |
| Anthrax Attack | October 2001 | ED visits for actual/possible anthrax exp. | Ad hoc case creation/data visualization | Clustered at Trenton NJ; prolonged peak | Supported by news articles and ad hoc study |
| Doctors' Strike | Feb 4–5, 2003 | Spike in ED visits | HWR | Strongest spike in 0–10 & 10–20 age groups | Confirm on web; found weather-related drop in mid-Feb |
| Clinton Effect | Sep 7–16, 2004 | ED visits for cardio exams | CPD | Middle aged men in affluent suburbs | Follow up to widely reported Bill Clinton hospitalization |
| Respiratory Distress | Aug 6, 2001 | ED visits with respiratory syndromic gp | KFC | Trenton NJ | Increase in "chest pain" |
| Trauma | Aug 28, 1997 | ED visits for trauma | KFC with covariates | NJ Shore, adult females | Open – Rough surf? |

FIG. 9

Multi-domain Anomaly Patterns

Example 1
If   score_(Alg=A) ( zip5=81506, ED, "respiratory" ) > 3.0 then
    Gather {
        events (neighbor 81506, ED or ELR, "respiratory" ),
        events ( state=CO, EPIZOO, "respiratory" )
    }
    Summarize { #anomalies; #events; Bayes probability }
    View {
        ED respiratory counts by zip5 within 100m of zip5=81506,
        flu cases nationwide by state,
        ELR respiratory counts by day for zip5=81506,
        EPIZOO by day for state=CO
    }

FIG. 14

Three sets of objects

Data sources (e.g., 1,2,3)
 – including primary, secondary, or tertiary data Generate

Data extracts (e.g., a,b,c)
 – E.g., a from 1, b from 2 & 3, c from 3

Apply

Algorithms (e.g. I, II, III, IV)
 – E.g., apply I & II to a; I & III to b; IV to c

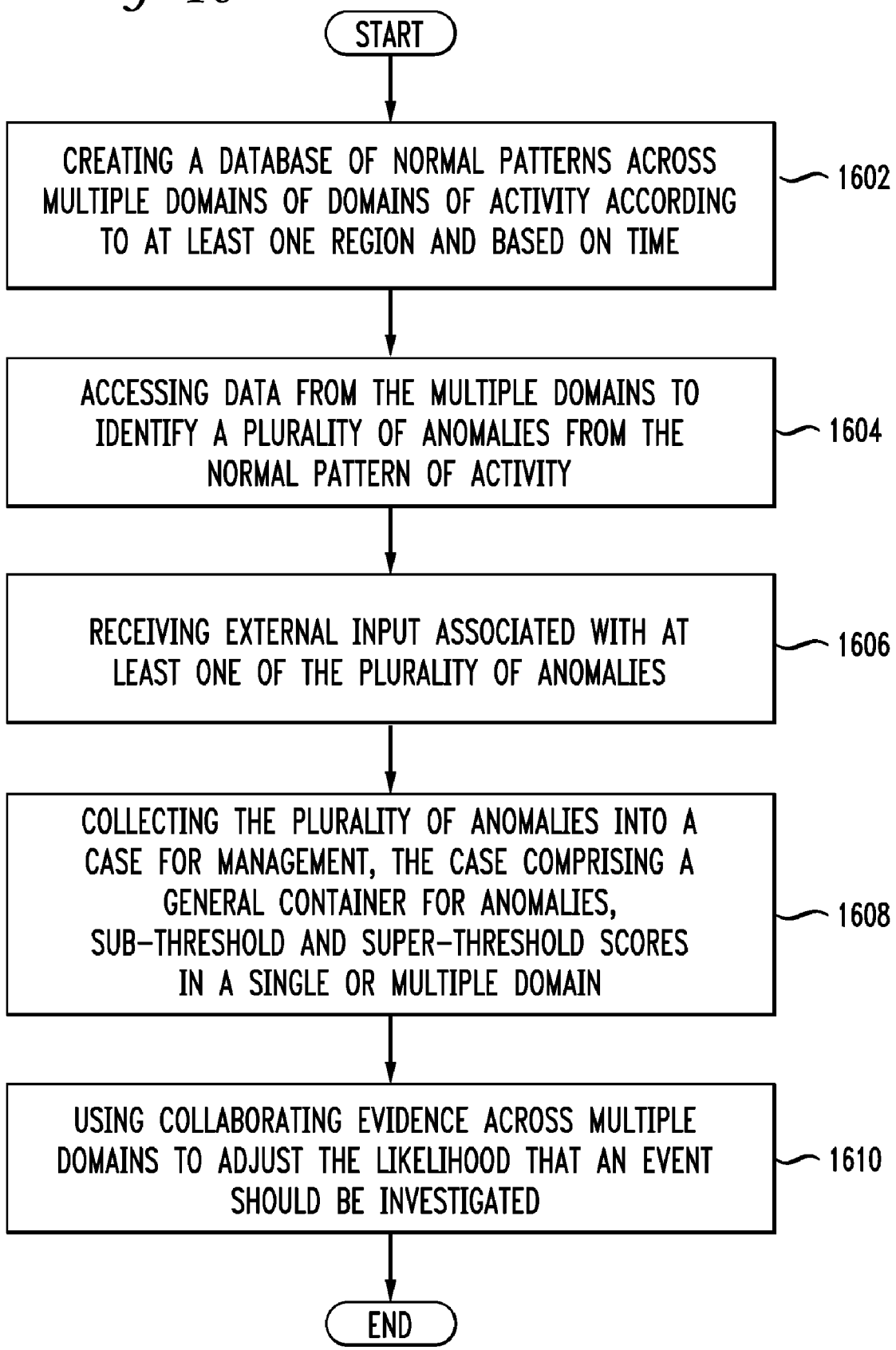

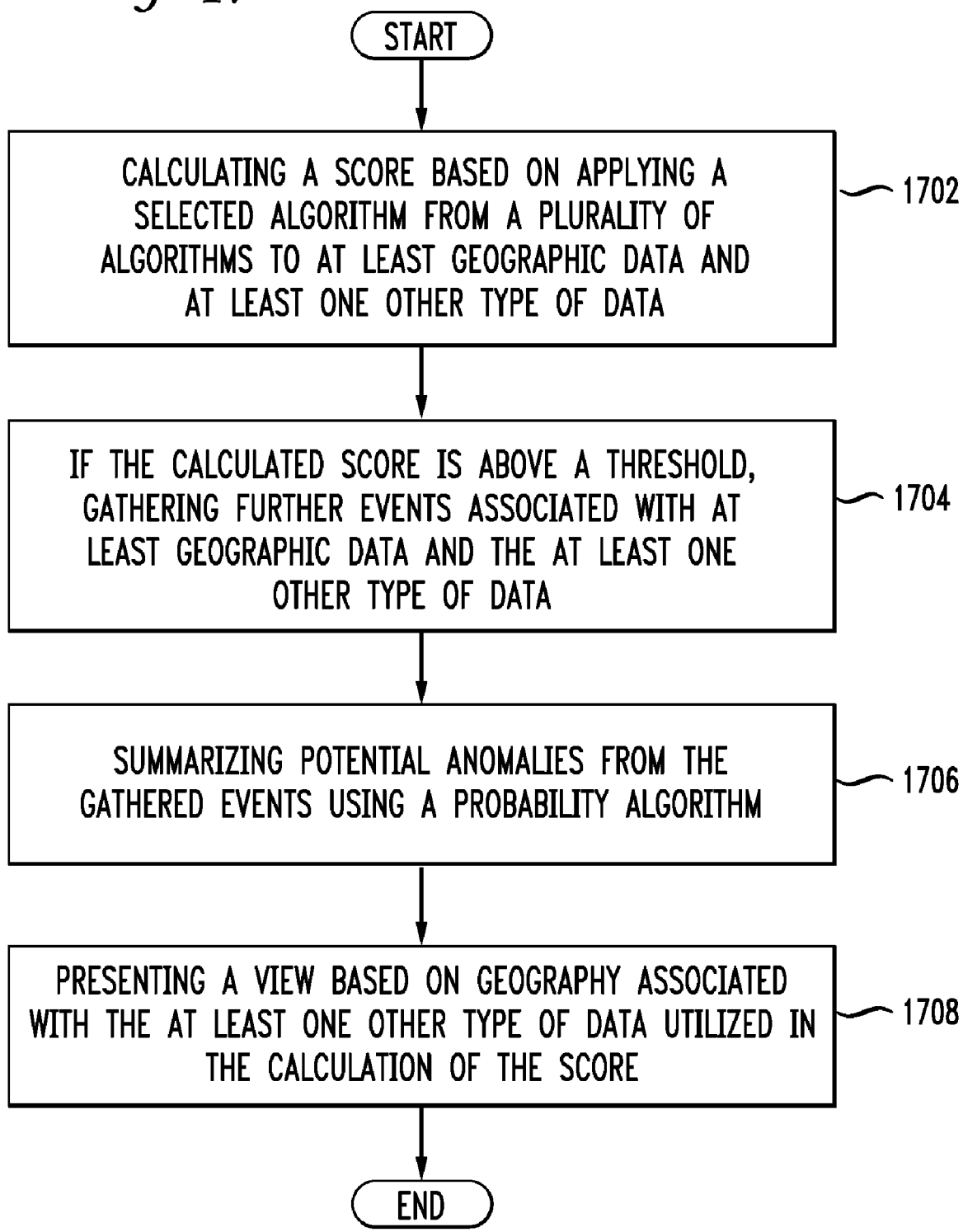

METHOD AND APPARATUS FOR MULTI-DOMAIN ANOMALY PATTERN DEFINITION AND DETECTION

CROSS-REFERENCE TO RELATED APPLICATIONS

This application is related to U.S. patent application Ser. No. 11/518,291 filed Sep. 8, 2006; U.S. patent application Ser. No. 11/086,820 filed Mar. 22, 2005; U.S. patent application Ser. No. 11/253,164 filed Oct. 18, 2005; and U.S. patent application Ser. No. 11/796,691 filed Apr. 27, 2007 the disclosure of which is incorporated herein by reference in their entirety.

BACKGROUND OF THE INVENTION

1. Field of the Invention

The present invention relates to pattern anomaly detection and more specifically to a method and apparatus for performing a multi-domain anomaly pattern definition and detection.

2. Introduction

Within the field of biosurveillance, there is a need to detect emerging diseases or other biological threats as early in the lifecycle as possible. This process is known as syndromic surveillance where experts study intermediate indicators related to diseases. It is estimated that hundreds of millions of dollars could be saved along with thousands of deaths avoided if early detection could be pushed back into the incubation period (i.e. pre or early symptomatic behavior) of a disease. There is a known positive effect of early detection with the effect of traditional disease detection. Statistics show that the number of victims that may die is greatly reduced when early surveillance and detection is available when compared with late detection. There is a need to provide a data fusion and accompanying analysis across varying data sources and varying data types or domains that could describe an anomalous event from potentially different geospatial and temporal perspectives.

SUMMARY OF THE INVENTION

Additional features and advantages of the invention will be set forth in the description which follows, and in part will be obvious from the description, or may be learned by practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth herein.

The present inventors understand how critical it is from both a health perspective as well as a financial perspective to provide as early as possible an indication of a potential outbreak. The detection window begins with data arriving at the system. The inventors attempt to move the detection of an event as close as possible to the data acquisition from the source. Additionally, having access to both pre-summarized data as well as query-driven summarization assists in early detection in view of historical base line data. As the volume of the data in the system grows, it is important that the detection system be both scalable and flexible. The present solution is preferably built on proven massively scalable technologies such as streamline analysis of over 400 million records per day times 300 plus different algorithm characterization and rules. System results should be measured based on effective knowledge representations from the data source. The inventors typically define "results" into the system to meet the goal of effective knowledge representation. Displaying "raw" data has value and also can be done quickly using the approach of the invention. Applying the appropriate data characterization and severity indicators along with combined data fusion landscape view is a very effective method and system of making results actionable.

Providing the proper venue for evaluating alerts is an important function addressed in a comprehensive manner supported by the "funnel" and the multi-domain anomaly pattern module (MDAP) discussed herein. An example funnel is shown in FIG. 6. All alerts whether generated by an anomaly detection engine, or in concert with other manual activities, are presented to the analyst for analysis and disposition by appropriate personnel.

In the anomaly detection framework all notes are routed to the collaborative event investigation module (CEIM). This module provides the subject matter experts (SMEs) to review the alert, explore the causes, facts and source data, compare analysis and other like events and engage the MDAP to help review indicators that might be present from other data sources. Some or all of these features may be automated. The CEIM also provides the tools to escalate the event up the chain, dismiss the event as a false positive or retain the event for further analysis and to see if other collaborating data is received.

During the investigative phase, which typically could last from moments to days, an active "life" will be presented to the knowledge base that can be called upon to display past data or similar event resolution decisions which will, over time, decrease the level of effort needed to review the anomaly. Average practice data may be gathered—such as normal visits to the doctor during flu season etc.

Upon event resolution, the assigned analyst will be asked to provide an in depth description of the event and actions taken. This will be subjective, but will provide the human perspective on why the anomaly was handled as it was and what knowledge and lessons learned can be gained from the event. This feedback may be used for two purposes: (a) storage in the knowledge data base for subsequent recall and (b) feedback to the sponsor system engineers and SMEs for potential adjustments to the algorithms operating parameters, rules engines and MDAP functions. This may occur through a web portal such as that shown as feature 624 in FIG. 6.

The concept for an MDAP arose out of an idea identified above to provide data fusion and appropriate analysis across a variety of data sources and varying domains that will describe an anomalous event from various geo-spatial and temporal perspectives. Each data source and type might describe events that when seen individually do not cross a threshold of interest, but when taken together may cross a threshold and trigger some kind of alert. By applying different statistical weights as well as threat and confidence parameters, the MDAP assists in the signal to noise ratio by suppressing signals that are actually false positives while enhancing ones that would have been ignored (false negatives) if not viewed from this multi-domain perspective.

The embodiments of the invention include an invention and an apparatus for performing multi-domain anomaly pattern definition and detection. The method embodiment comprises a method of performing multi-domain surveillance. The method comprises creating a database of normal patterns across multiple domains of activity according to at least one region and based on time, accessing data from the multiple domains to identify a plurality of anomalies from the normal patterns of activity, receiving external input associated with at least one of a plurality of anomalies, and collecting the plurality of anomalies into one or more cases for management. The "case" may comprise a general container for anomalies, sub-threshold and super-threshold scores, for preferred summaries and visualizations, for references to ancillary data, for URL's to pertinent information, to notes entered by users, and to descriptions of context. The contents of the case are in a single or multiple domains and uses collaborative evidence across the multi-domains to adjust a likelihood that the event should be investigated. This invention may provide a multi-domain anomaly pattern module (MDAP) that may be utilized in any area of anomaly detection, including but not at all limited to biosurveillance.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 5 illustrates an anomaly detection and case management approach;

FIG. 6 illustrates an example anomaly detection architecture and SOA framework;

FIG. 7 illustrates a table of interoperative modules for early event detection;

FIG. 8 illustrates sample events in event detection visit data;

FIG. 9 illustrates a multi-domain anomaly pattern analysis;

FIG. 14 illustrates example sets of objects used in a MDAP;

FIG. 16 illustrates a method embodiment of the invention; and

FIG. 17 illustrates another method embodiment of the invention.

DETAILED DESCRIPTION OF THE INVENTION

Various embodiments of the invention are discussed in detail below. While specific implementations are discussed, it should be understood that this is done for illustration purposes only. A person skilled in the relevant art will recognize that other components and configurations may be used without parting from the spirit and scope of the invention.

The present invention relates to an improved method of multi-domain pattern detection. A computer system may process some or all of the steps recited in the claims. Those of ordinary skill in the art will understand whether the steps can occur on a single computing device, such as a personal computer having a Pentium central processing unit, or whether some or all of the steps occur on various computer devices distributed in a network. The computer device or devices will function according to software instructions provided in accordance with the principles of the invention. As will become clear in the description below, the physical location of where various steps in the methods occur is irrelevant to the substance of the invention disclosed herein. Accordingly, as used herein, the term "the system" will refer to any computer device or devices that are programmed to function and process the steps of the method.

Figure 1:
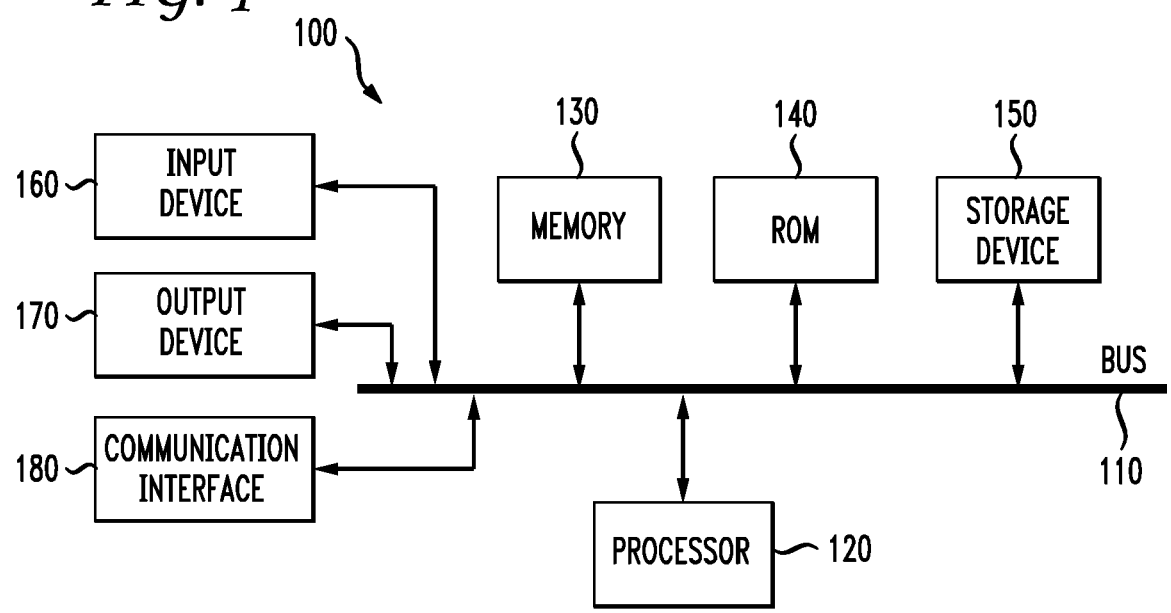
FIG. 1 illustrates a basic system embodiment of the invention.

One embodiment of the invention relates to a system for performing multi-domain anomaly pattern definition and detection. With reference to FIG. 1, an exemplary system for implementing the invention includes a general-purpose computing device 100, including a processing unit (CPU) 120 and a system bus 110 that couples various system components including the system memory such as read only memory (ROM) 140 and random access memory (RAM) 150 to the processing unit 120. Other system memory 130 may be available for use as well. It can be appreciated that the invention may, and typically does, operate on a computing device with more than one CPU 120 or on a group or cluster of computing devices networked together to provide greater processing capability. The system bus 110 may be any of several types of bus structures including a memory bus or memory controller, a peripheral bus, and a local bus using any of a variety of bus architectures. A basic input/output (BIOS), containing the basic routine that helps to transfer information between elements within the computing device 100, such as during start-up, is typically stored in ROM 140. The computing device 100 further includes storage means such as a hard disk drive 160, a magnetic disk drive, an optical disk drive, tape drive or the like. The storage device 160 is connected to the system bus 110 by a drive interface. The drives and the associated computer readable media provide nonvolatile storage of computer readable instructions, data structures, program modules and other data for the computing device 100. The basic components are known to those of skill in the art and appropriate variations are contemplated depending on the type of device, such as whether the device is a small, handheld computing device, a desktop computer, or a computer server.

Although the exemplary environment described herein employs the hard disk, it should be appreciated by those skilled in the art that other types of computer readable media which can store data that are accessible by a computer, such as magnetic cassettes, flash memory cards, digital versatile disks, cartridges, random access memories (RAMs) 130, read only memory (ROM), a cable or wireless signal containing a bit stream and the like, may also be used in the exemplary operating environment.

The essential input and output features of the system include one or more interfaces to input data into the system, which may includes network connections and readers for physical media. Software protocols are available to input data in both raw file or streaming format or through read access to an external database. The system includes one or more databases internally also. Similarly, the system includes one or more interfaces to output data from the system, which may include network connections and writers for physical media.

Software protocols are available to output data in both raw file or streaming format or through write access to an external database. User interaction with the system is supported by both network connections, with various accompanying software protocols reflecting current practice, and input mechanisms for the computing system. To enable user interaction with the computing device 100, an input device 160 represents any number of input mechanisms, such as a microphone for speech, a touch-sensitive screen for gesture or graphical input, keyboard, mouse, motion input, speech and so forth. The input may be used by the presenter to indicate the beginning of a speech search query. The output device 170 can also be one or more of a number of output means. In some instances, multimodal systems enable a user to provide multiple types of input to communicate with the computing device 100. The communications interface 180 generally governs and manages the user input and system output. There is no restriction on the invention operating on any particular hardware arrangement and therefore the basic features here may easily be substituted for improved hardware or firmware arrangements as they are developed.

As introduced above, the multi-domain anomaly pattern module (MDAP), according to various aspects of the invention, provides important contributions to the field of anomaly detection and various aspects of the MDAP rule will be addressed herein. For example, several aspects which will be addressed include: (1) Sustaining 'patterns of interest' generated either automatically or from manual input. These multi-domain patterns would persist in the MDAP data store and enable comparisons to new data received. Should a similar threat pattern be emerging in another location or over an extended time period as specified by the subject matter expert (SME), the MDAP functions to alert the proper investigators; (2) The collaborative event investigation module (CEIM), also know as a case manager, and the rules for combining anomalies from different domains into a single case for investigation; and (3) The third use of the MDAP is to provide feed-back to a core anomaly detection engine that could form the basis for adjustments to settings of one or more algorithm or algorithm operating parameters (AOP) and for algorithm enhancements.

Figure 2:
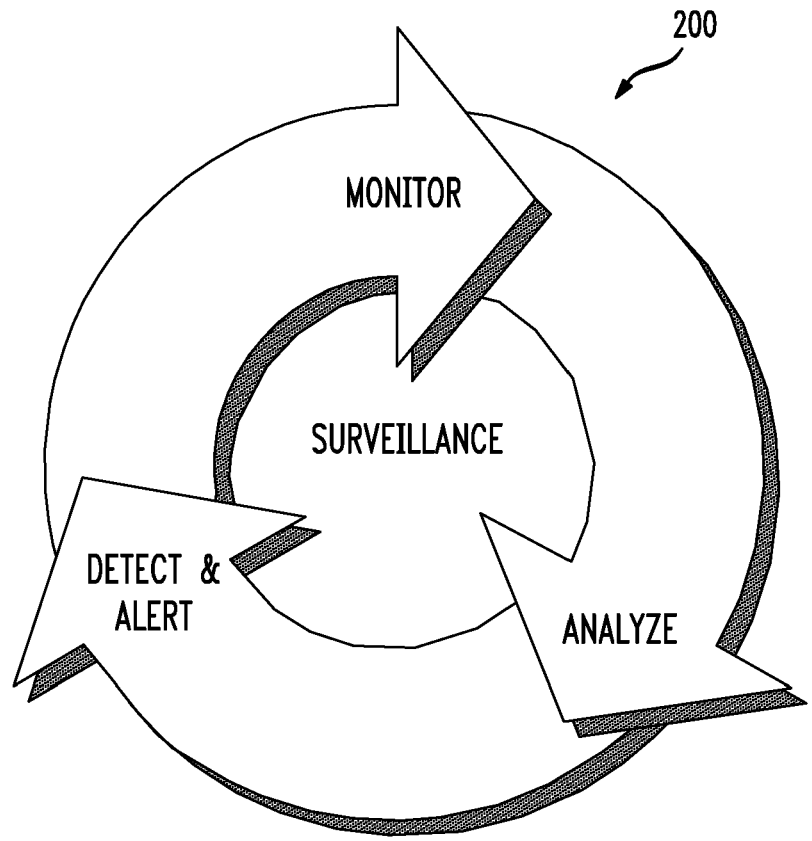
FIG. 2 illustrates the basic components of an early detection cycle.

FIG. 2 illustrates the basic early detection cycle 200 which includes a cycle of monitoring, analyzing and detecting anomalies and providing the appropriate alert all surrounding the concept of surveillance. Particularly in the area of biosurveillance, this typically refers to the automated monitoring and existing health and related data sources to identify trends that may indicate naturally occurring or intention disease outbreaks. Example sources of data which may be gathered from multiple domains include, but are not limited to, laboratory requisitions and test results, hospital ER complaints and admissions, school or work absenteeism, pharmaceutical or medical device or medicine sales, doctor office visits, animal or agriculture indicators such as reports from veterinary clinics, air and water sensors, monitoring of websites such as WebMD.com, intelligence agency feeds and so forth.

Traditional biosurveillance approaches include confirmed occurrences of notifiable conditions which may trigger reports to various government entities such as State Departments of Health or Centers of Disease Control. In some cases, entities have attempted automated biosurveillance which establish a process to organize the monitor health data for timely and reliable identifications of events of health concern. Disclosed herein is an aspect of automated biosurveillance which provides a fast, accurate, comprehensive and diverse application of statistical anomaly detection methods and the various engines and the MDAP. Another biosurveillance approach is a syndromic surveillance approach which recognizes patterns and possible diverse data sources such as ER, lab tests, absenteeism, chief complaints from clinics and hospital visits, biochemical exposure, veterinary data, environmental data and so forth.

The challenges in biosurveillance include data acquisition. Across these multiple domains there are non-uniform data standards and cross-domain analysis which needs to occur. Furthermore, cross jurisdictional analysis such as from state-to-state, county-to-county or place-to-place (city-to-city) also presents multiple challenges. For example, processes related to the collection, contents, formatting, sharing, and retention of health and other data need to be put in place and harmonized. Another issue with data acquisition is the need to manage massive amounts of data. The approach discussed herein also addresses a challenge in biosurveillance which is scalability. The system needs to simultaneously load and analyze millions of records from diverse sources such as noted above, hospitals, laboratories, doctor offices, schools, retail pharmacies, environmental centers, the intelligence community and so forth. The bandwidth necessary to rapidly and securely route data feeds from diverse locations without large incremental expenses is an issue as well as the need to use proven network engineering capabilities. A purpose of the MDAP disclosed herein is to provide rapid anomaly detection that reduces false alerts without masking true signals. One of the methods of providing the anomaly detection is a parallel comparison of anomaly indicators from multiple sources or multiple domains and also algorithms that provide rapid pattern detection as millions of records are captured. The present invention also enables the critical detection of unexpected anomalies or patterns beyond what may be anticipated based on current data.

An aspect of the invention is to collect the various data from multiple domains into a case for management. Accordingly, the system provides effective case management which includes investigative tools to research potential threats in realtime and includes scalable, statistical and geo-spatial visualization tools available to view the threat landscape. The system provides secure access to anomaly case details as an event unfolds. For example, the system will be compatible with the Health Insurance Portability and Accountability Act (HIPAA), legislation dealing with the security and privacy of health data. The "case" may comprise a general container for anomalies, sub-threshold and super-threshold scores, for preferred summaries and visualizations, for references to ancillary data, for URL's to pertinent information, to notes entered by users, and to descriptions of context. The contents of the case are in a single or multiple domains and the case uses collaborative evidence across the multiple domains to adjust the likelihood that the event should be investigated. This invention may provide a MDAP that may be utilized in any area of anomaly detection, including but not limited to bio surveillance.

Figure 3:
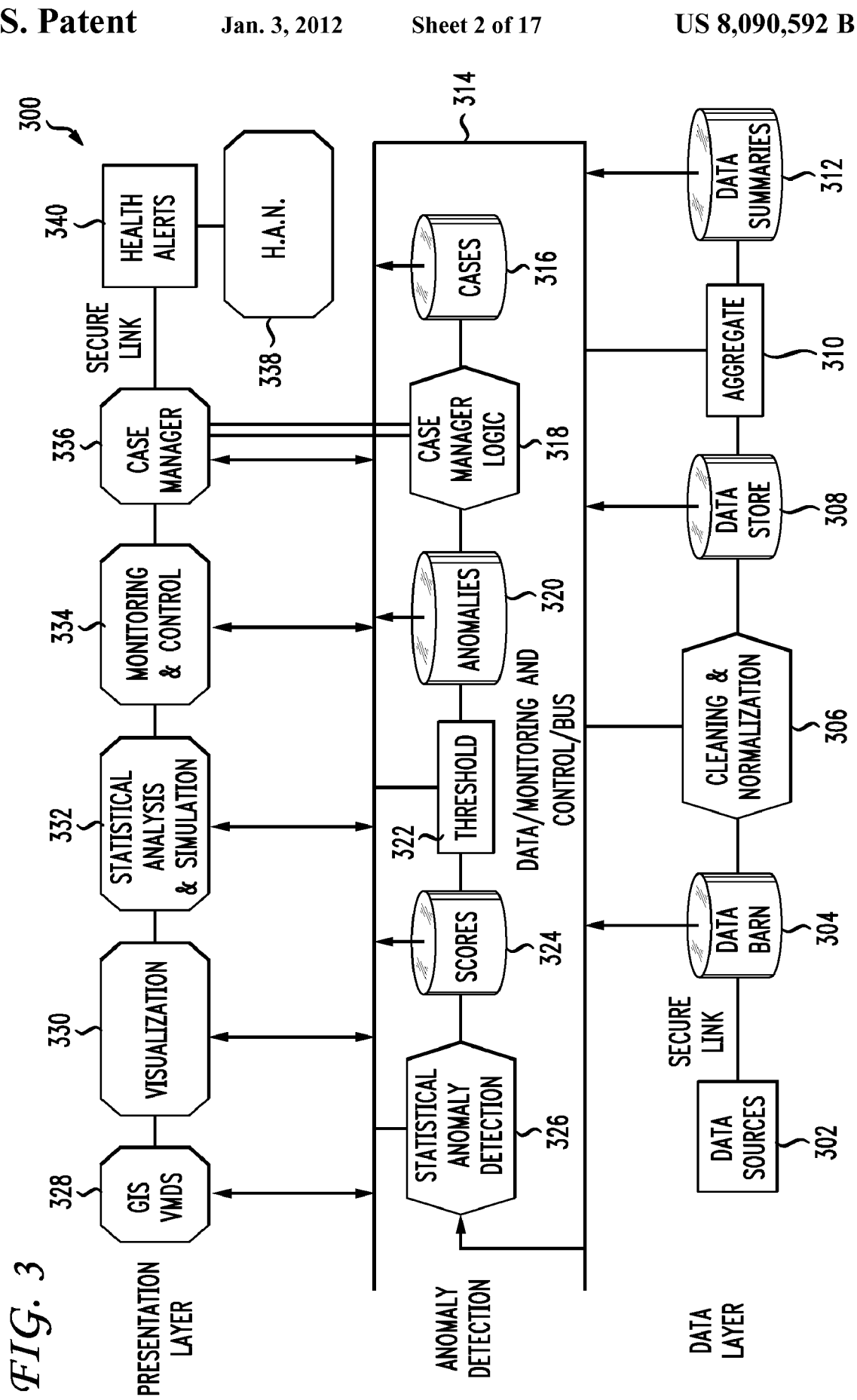
FIG. 3 illustrates an architecture for early event detection in health care data.

FIG. 3 illustrates an example architecture for early event detection based on health care data. This architecture provides a comprehensive health and environmental data approach which includes geo-temporally and demographically diverse data. The architecture 300 provides efficient and realtime large scale information processing and comprehensive and tunable anomaly detection algorithms. This is a flexible platform for investigation and management of anomalies and cases and includes alert distribution and management provisions. The lower third of the architecture 300 includes a data layer which provides the basic gathering of data from various data sources 302 and through a secure link provides a data barn 304 which can also go through a cleaning and normalization process 306. Such a process can generate a data store 308 that may be aggregated 310 into data summaries 312. The middle third of the architecture 300 is the anomaly detection layer that receives data from the data layer and performs a statistical anomaly detection function 326 and generates scores 324 which are evaluated against one or more thresholds, including the use of smart thresholds 610, which may be, for example, sub-threshold or super-threshold scores to identify anomalies 320. The anomalies are collected into a case which is organized and managed according to case manager logic 318 and stored in the case table or tables 316. The upper third of the architecture 300 is the presentation layer which includes a Geographic Information System (GIS) which supports Visualization of Massive Data Sets (VMDS) 328, and stores and analyzes the highly complex spatial and topological networks. The GIS VMDS communicates with a further visualization tool 330 and a statistical analysis and simulation tool 332. The simulation tool 332 communicates with monitoring and control modules 334 which also communicate with a case manager 336 which via a secure data link can communication health alerts 340 and communication with a Health Alert Network (H.A.N.) 338. The H.A.N. acts as a secure communication and alert reporting system that can rapidly disseminate info via a range of devices that include, but are not limited to, telephones, PCs, PDAs, cell phones, and other means.

Data communication within the architecture 300 is through a data bus 314, except for the data sources 302 which communicate to the data barn 304 via a secure link, and except for the health alerts 340 and H.A.N. 338 modules which communicate via a secure link to the case manager 336. One use of the data bus 314 is to transport data to and from any of the stored tables, data barn 304, data store 308, data summaries 312, scores 324, anomalies 320, and cases 316, and any other tables that are included in an implementation, for example for external identified anomalies 620, or a knowledge base 626, or inputs via a web portal 624. Data on the data bus from these tables can provide input to any one or all of the process modules, including cleaning and normalization 306, aggregation 310, statistical anomaly detection 326, thresholds 322, GIS and VMDS 328, visualization 330, statistical analysis and simulation 332, and the case manager 336 using case manager logic 318 that includes the MDAP capability. A second use of the data bus is for monitoring, whereby summaries of the contents of the data tables, and summaries of the activity associated with each of the tables and process modules, including input and output totals, are provided to the monitoring and control module 334. A third use of the data bus is for control, whereby operating parameters are set, typically in the monitoring and control module 334, for each of the process modules, and the case manager logic 318 is established and tuned. These uses of the data bus provide useful and valuable flexibility and power in using this architecture for early event detection, including monitoring, control, and analysis different from the canonical flow from data sources 302 to data barn 304 to cleaning and normalization 306 to data store 308 to aggregation 310 to data summaries 312 to statistical anomaly detection 326 to scores 324 and so forth. Further features of the architecture, which support multiple domain anomaly patterns, are called out in FIG. 6 and in its associated description.

Figure 4:
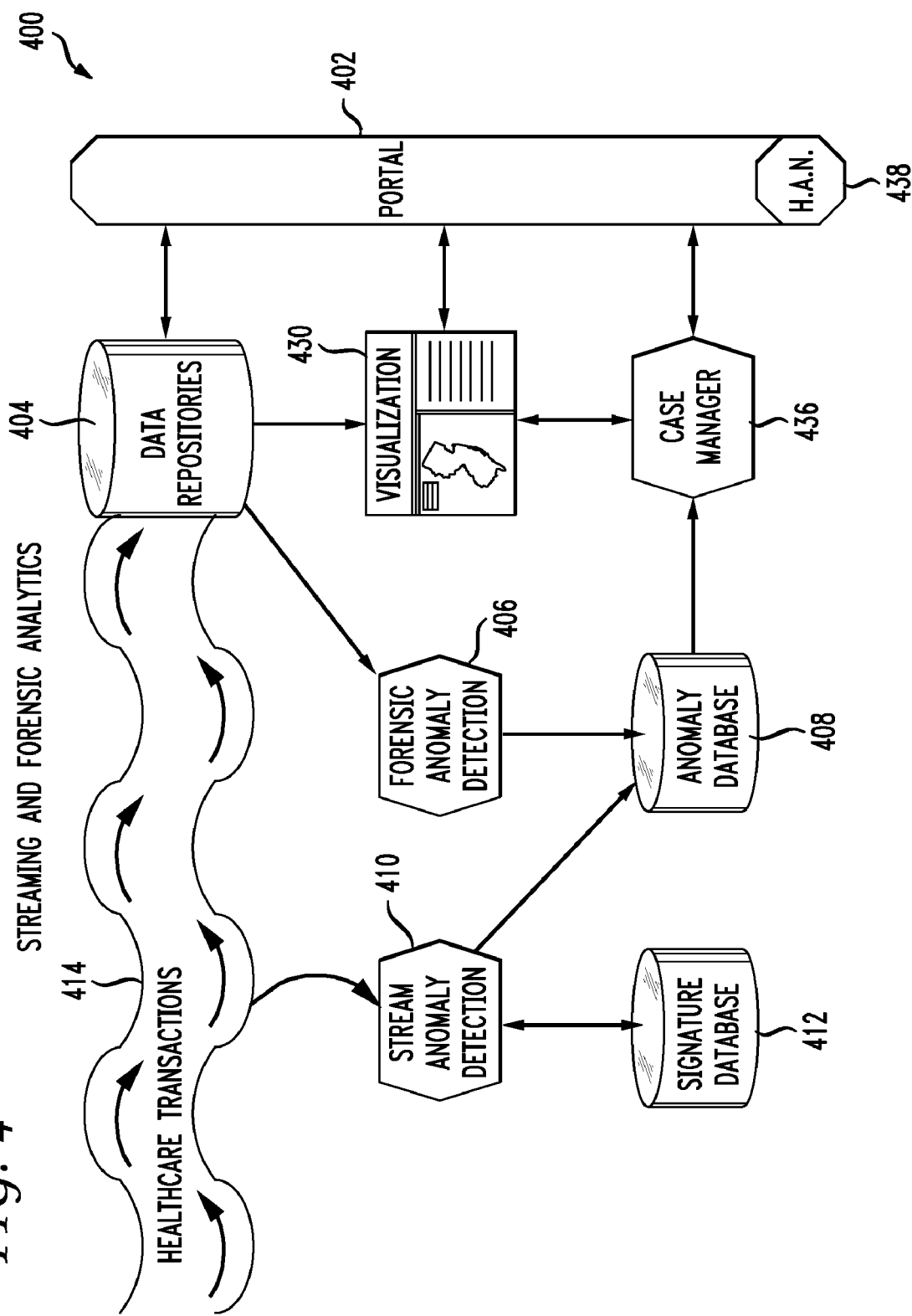
FIG. 4 illustrates a streaming and forensic analysis approach.

FIG. 4 illustrates a streaming and forensic analysis approach. The example provided herein is a data domain of healthcare transactions 414. The data associated with healthcare transactions flows into a data repository 404. The stream of data from healthcare transactions is communicated to a stream anomaly detection module 410 which communicates with a signature database 412 and provides data to an anomaly database 408. Corresponding to single transactions or to aggregates of transactions, for example hourly counts for a hospital emergency department of patients with a specific complaint, the transactions trigger retrieval of the historical signature for that type of transaction from the signature database 412. The transactions are compared to the historical signature and may generate an anomaly; if not the signature is modified with the transactions and the signature database updated. For efficiency, the signature database might be kept in random access memory (RAM) and not solely on disk. Similarly, from the data repository 404 information is provided by way of forensic anomaly detection 406 which output is also communicated to an anomaly database 408. The combined data stored in the anomaly database 408 is communicated to the case manager 336 which communicates with visualization tool 330 and the portal 402. The visualization tool 330 and the case manager 336, in connection with the data from the data repository 404, communicate with the portal 402 and the H.A.N. 338. The visualization tool also receives data from the data repository 404 to enable it to provide the appropriate visualization for experts to determine if an event is occurring.

FIG. 5 illustrates an anomaly detection and case management approach with various modules. The approach 500 includes the date ingestion transformation and storage component 504 which includes the data barn 304 which communicates raw data to a cleansing and transformation module 306 which operates on the raw data to enable it to be stored in the data store 308 for further use. An anomaly detection engine 502 provides data summarization and statistical anomaly detection as well as bolt-on anomaly detection. This engine provides a score database and includes smart thresholds and also generates an anomaly database.

A collaborative event investigation module 504 includes case creation logic in a case database. It provides multi-domain anomaly pattern analysis as well as generating a pre-alert message and provides case management. Other aspects of anomaly detection case management also includes security management 506, a control database and a management portal 508 as well as a visualization drill down and GIS, reporting and ad-hoc analysis module 510. Finally, the end result of all of these processes is a determination of when an alert should occur to alert 512 authorities of a threatening event.

FIG. 6 illustrates an example anomaly detection architecture and service oriented architecture (SOA) framework for a massively-scalable anomaly detection and threat management system. This may also be termed as the "early event detection funnel" or more briefly "funnel" 600. The top layer 602 of the funnel encompasses the data management component in which data is ingested from various sources such as environmental, human sources, animal sources, plant sources as well as food supplies. This data management component may operate on data streams 414 or on data loaded into a data repository 404. The next layer 604 illustrates data selections and extractions that are performed on the data from the various sources. The extracted data may include a simple time series or an array of time series. This layer 604 may include an analysis which produces relational graphs between the various multiple domain pieces of data and may also include entity extraction algorithms which categorize concepts from the multiple domains of data. Layer 606 illustrates various anomaly detection algorithms such as HWR, KFC, CPD, NGAD, anomaly detection rules, and one or more "bolt-on" algorithms from external sources. Layer 608 illustrates the reception of scores from these various anomaly detection algorithms. The scores are compared against smart thresholds 610 which may include sub-thresholds as well as super-thresholds in a single or multiple domain. Layer 612 is fundamental for multi-domain anomaly pattern generation and analysis. In layer 614, a module containing case generation logic and multi-domain anomaly patterns combine related anomalies into "smart" containers called cases. The anomalies combined into a particular case may be related by location, such as Seattle or San Diego, or particular possible illnesses such as Avian Flu or the West Nile Virus or the Hanta Virus, or by both illness and location such as Botulism in California, and so on.

External events may be included in the analysis in layer 612 such as unique or notifiable events or external captured anomalies 620 such as tertiary data from public healthcare agencies or labs such as sentinel labs. The data from layer 612 is provided to a collaborative event investigative module (CEIM) 614 which facilitates a more in-depth, machine-assisted, human look at the data to investigate certain possible events. The key multi-domain anomaly pattern functionality is provided in layer 612 supported by the CEIM layer 614 as well as the other layers.

The output from the collaborative event investigative module 614 is sent to a knowledge base 626 which provides feedback to each of layers 602, 604, 606, 608, 610 and 612 to adjust and improve the analyses in at least one of these layers. The output from the CEIM 614 is also provided to a data visualization, analysis, and fusion (DVAF) layer 616 which provides a set of interfaces and views into the data including to the CEIM and can output data including analytical results. This DVAF layer 616 may be accessed through a web portal, or some other system that would be known in the art, by partners and subject matter experts (SMEs) as well as by government agencies such as DHS, NOC, NBSG, AIC, CMC, CDC, DHHS, Coast Guard, and NBSG. Another function of the DVAF layer 616 is to issue a public alert 618. Custom analytics from this layer may also be provided to earlier layers 602, 604, 606, 608, 610 and 612. The approach of FIG. 6 provides a sample application of the funnel which includes the MDAP approach to biosurveillance.

FIG. 7 illustrates a table of interoperative modules for early event detection. One or more of these modules may be utilized in various aspects of the invention. The left column provides a description of a particular function in the example architecture, for MDAP, and the funnel approach. The next column illustrates a technology module which may be used to implement that particular functionality. The third column illustrates a description of the module and what it does in the overall event detection analysis. The last column provides illustrated interoperability and language in which a particular module may be implemented. This table provides some more basic information and would teach one of skill in the art some of the exemplary modules or known software or programming languages which may be used to program and integrate the various components needed to handle the multi-domain anomaly pattern detection approach disclosed herein.

Next, we discuss several examples of various data elements that are used for interoperability of the data from the various domains. For example, geographical locations may be referenced in a five-digit zip code or a three-digit zip code including such information as county, state, hospital ID or a city or town. Information may be provided about whether the data is associated with a patient or a health provider. There are a number of medical indicators that may be used, such as data associated with a syndromic group: respiratory, gastro-intestinal, fever, botulism-like and so forth. Data may refer to ICD9 codes and code groups: 78900, 8264, 834xx, etc. The data may also comprise patient records for visits to a hospital emergency department, including chief complaint content such as abdominal pain, pain in left leg, etc. Temporal data elements may be used such as the earliest and latest patient visit date, the date of data loading, the date of statistical analysis, and so forth. A list of covariates may include such data as age, sex, length of stay in hospital, severity described and so forth. The above provides an example of the various data elements which may be used to receive data from the multiple domains to provide a list of statistical measures and their descriptions which include identifiers for data, algorithms, security and access.

FIG. 8 illustrates a chart of sample events in event detection (ED) visit data as provided by Emergency Medical Associates of NJ. For example, an event labeled meningitis exposure is illustrated in the first row of FIG. 8. The data includes when the visit occurred, which in this example is Jul. 17-19, 2004. Visits to the hospital for meningitis were detected by a change point detection (CPD) algorithm in the time series of chief complaints registered by patients as they were making hospital visits, and also using the KFC algorithm. The features of the event include variate information that might be used creating cases, for example in layer 612 of the funnel. For the first row of FIG. 8 the location is Livingston, N.J., and the event affected campers and parents. The incident management column summarizes the potential results of analysis in the CEIM layer 614 of the funnel. A five-year old day camper died of bacterial meningitis. Other example events in FIG. 8 are labeled anthrax attack, doctor's strike, the "Clinton effect", respiratory distress, and trauma. The chart 800 of FIG. 8 illustrates various types of events and data which may be utilized in the multi-domain anomaly pattern detection.

FIG. 9 illustrates an example of pseudo code for multi-domain anomaly patterns. In this example, the pattern includes a condition, followed by gather, summarize, and view actions. The condition compares a score, for example from the score tables in layer 608 in FIG. 6, to a threshold, in this example, 3.0. The score is for a specific algorithm, "A", a specific zip5, 81506, and for emergency department visits for patients with the respiratory syndrome. The pattern is applied repeatedly in time, for example each day. The MDAP in FIG. 9 might be for the single instance of zip5=81506 or might be a template for each zip5. When the pseudo code is a template, we might rewrite it as zip5=z where z ranges over all zip5 codes in the US.

The predicates in the pseudo code of the condition in the pattern in FIG. 9 must determine the truth or falsehood of the condition completely. For example, the zip5 81506 might be the location of the patient's home, of the patients insurance or billing address, of the emergency department, or some combination of these three. The reference to ED might encompass a specific emergency department, or multiple EDs, and might include just hospitals or hospitals and clinics. Further, there are multiple ways in which respiratory syndrome is defined using a classifier; two specific classifiers are the ICD9 code classifier from the CDC available at www.cdc.com, and a chief-complaint classifier based on n-grams developed by a group at AT&T including one or more of the present inventors and filed for patent. Collectively, the set of predicates for a true condition defines an anomaly.

When the condition is true, the MDAP prescribes a set of actions, including gather, summarize, and view actions. These actions are formulated to actively collect data both essential and relevant to understanding why the condition is satisfied, in the example the condition being that the score exceeds the threshold. These data, which further include the anomaly and its predicates, are collected into a container called a "case"; a case includes raw data, statistical summaries, the results of statistical analyses, graphical visualizations, annotations, the results of additional programmed or ad hoc analyses, and so forth. The initial creation of the case is according to the MDAP. The case contains information that can be conveniently used to support human analyses.

The analysis of a case may include multiple steps of human analyses, by the same or different analysts, and machine computation ordered explicitly or as actions according to the MDAP. For example, the MDAP may include two or more phases, where the condition described as human analysis of a case with the possible result of "interesting" (as distinct from "no further analysis necessary") triggers machine computation actions according to the MDAP that are collectively much more in depth than the original machine computations.

The example of FIG. 9 illustrates a single anomaly triggering creation of a case. The relationship of anomalies and cases can be more complex. For example, a case labeled respiratory in zip5=81506 may include data from multiple anomalies and the associated actions, possibly anomalies from different times in say a 4 week time period, or anomalies from zip5 region's that are neighbors to 81506 or syndromes related to "respiratory". The discussion of this paragraph makes plain that an MDAP encompasses more complex patterns than exemplified in FIG. 9.

The MDAP actions include but are not limited to "gather", "summarize", and "view". In the example, data gathered on some basis which may include neighboring zip codes, including information from the state. The emergency department (ED) and laboratory data (ELR) are also gathered. Events from the state are also gathered for animal related (EPIZOO) respiratory issues. The score mentioned above may be a score that is associated with domains, such as human health, animal health, climate, and so forth, as well as with such factors as zip code, state, municipality and so forth, and may involve pulling data from such sources such as the emergency department and human and animal respiratory data. A count may be gathered to respiratory cases in that zip code or other parameter for admissions to the emergency department. The count may be computed in various ways. For example, how to identify the respiratory patient may vary. In one case, this may be done by using ICD9 codes which may define a respiratory case as a patient being in the respiratory syndrome group if they have one of a number of ICD9 codes.

Other codes may also be utilized and may also be proprietary such that further analysis must be done. For example, particular hospitals or states may have particular codes that need to be transformed in the analysis to a common code set with associated descriptions. The UMLS software and database library provides one set of tools for doing this. Various codesets include ICD9 codes, used currently in the USA for diagnosis and procedures, ICD10 codes, used internationally and likely in the USA also in the future, CPT4 codes, and so forth. In another example, ICD9 codes are not used. Whereas, typically, the ICD9 codes are entered by doctors, in the normal course of an emergency department visit, however, a chief complaint is obtained at admission from the patient or the patient's companion. One or more ICD9 diagnosis and procedure codes will be assigned later, even when the established protocol is to generate ICD9 diagnosis codes as quickly as possible. For example, some ICD9 codes may not be available until tests are performed and the results of lab analysis returned. Thus an hour or two may have gone by at minimum, and every minute may count in a crisis. Thus, one possible source for raw data may be retrieved directly from patient chief complaint information. In this case, a different analysis may apply inasmuch as a particular text description generated by a patient or the patient's companion will obviously differ in content and medical precision from the codes entered by a doctor who is trained in diagnosis and coding diagnosis. When using patient chief complaint information, there may be algorithms which may be used to classify the chief complaint. For example, to determine whether the complaint indicates a respiratory syndrome or not, the appropriate classifier may need to be trained in order to classify from chief complaint text to syndrome.

In summary, for the example pattern in FIG. 9, when in the condition component the score exceeds the threshold then the system performs several actions, for example gather, summarize, and view actions. The system gathers information which may include counts or listings of detailed data from neighboring zip codes, emergency department and laboratory data on respiratory issues. The algorithm gathers the data, produces a summary, and identifies anomalies of a number of events, such as number and zip codes of patients and uses various known probability analysis, such as base probability to compare what is observed to what the system expects to observe. In this example algorithm, other events such as in the state of Colorado, the EPIZOO database is also analyzed, which database is collected under the Department of Agriculture for animal data. This data may be shown in maps or tables and presented in any way. The data is summarized and presented in a view for experts to study.

Next, an alert generation component, also known as case management, involves detecting case anomalies by diverse methods covering various geographies and medical conditions. A case manager is an effective tool to organize anomalies into cases and to support investigation. There are several aspects of case management. First, it serves as a focal point of user interaction. The tool allows experts, such as public health officials and epidemiologists to examine and evaluate anomalies efficiently and to decide how to act upon them. A case may contain any number of anomalies and anomalies may belong to several different cases. Accordingly, the anomalies are grouped into cases but not exclusively. A case management approach allows users to manage and explore these cases and drill down into details, such as root causes, anomalies and underlying data. The case management tool allows users to visualize data associated with the cases and the anomalies, and to take actions to dismiss or annotate cases. It also enables users to link to notification and loading modules if necessary. The technology in the example of a case management tool uses mature java-based toolkits developed and used for realtime case management applications such as fraud network or network monitoring.

Figure 10:
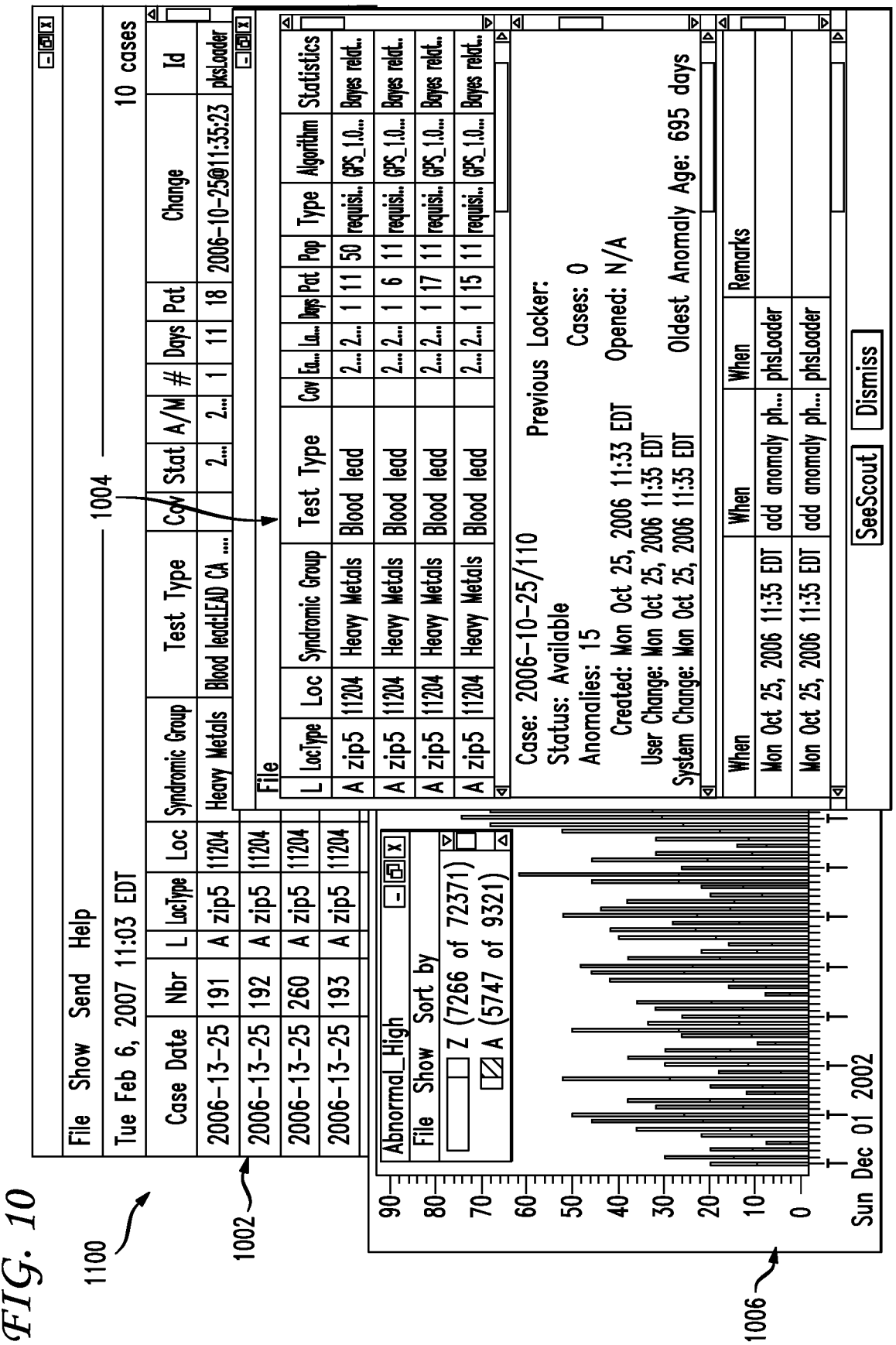
FIG. 10 illustrates a user interface for an anomaly investigation.

FIG. 10 illustrates an example user interface for anomaly investigation. A case work list window 1002 illustrates a summary of each case in a specific syndromic group. Window 1004 illustrates anomalies and case details as well as events for a selected case. Window 1006 illustrates a dynamic visualization of the data detail for a selected case which may be utilized by experts for detailed investigation and to generate a public health alert, if needed.

Figure 11:
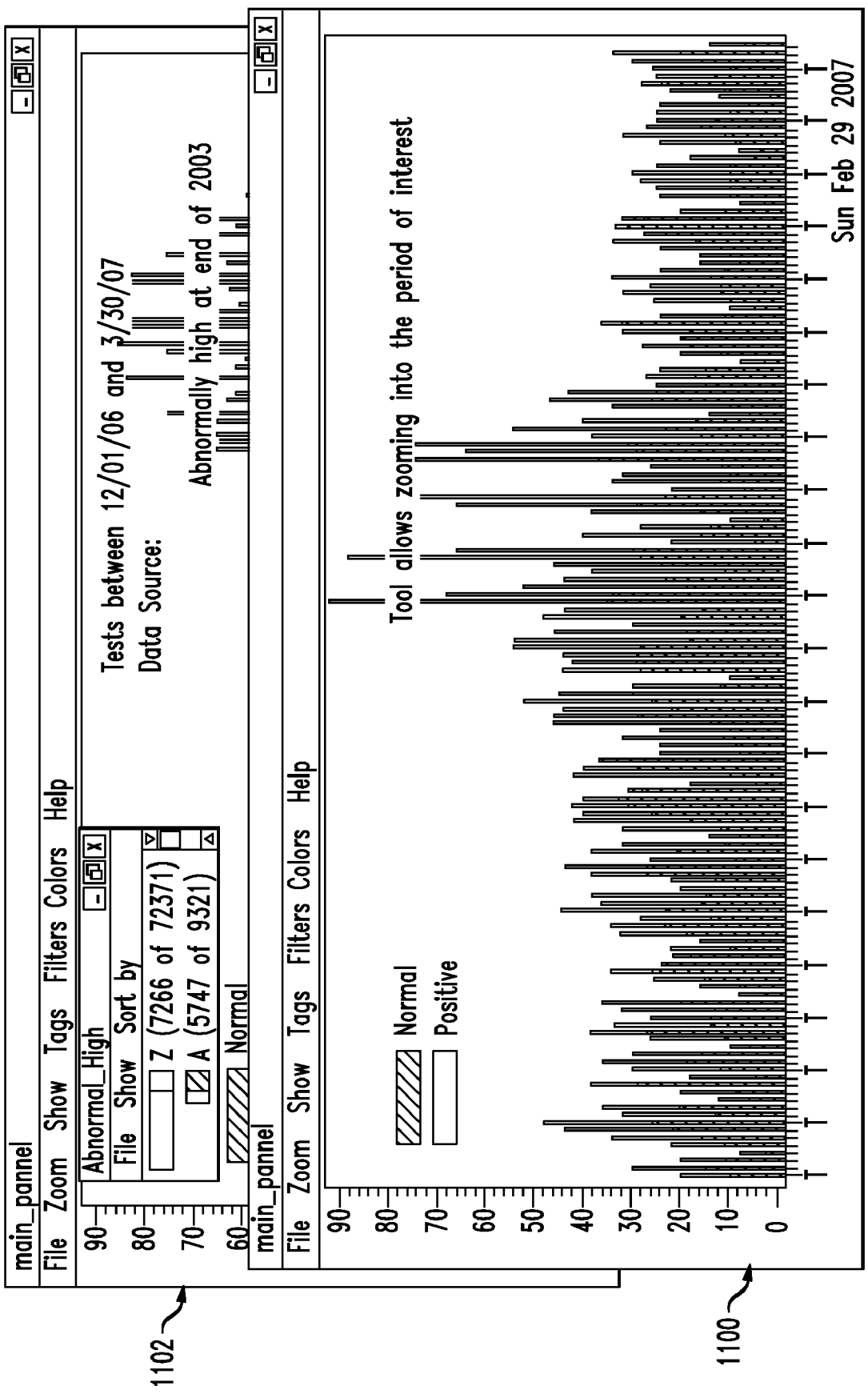
FIG. 11 illustrates user interfaces for visualizing and exploring time-series data.

FIG. 11 illustrates windows 1100 and 1102 which illustrate a visualization tool for exploring time-series data. The tool allows zooming into a period of interest and allows users to be able to visualize abnormally high data.

Figure 12A:
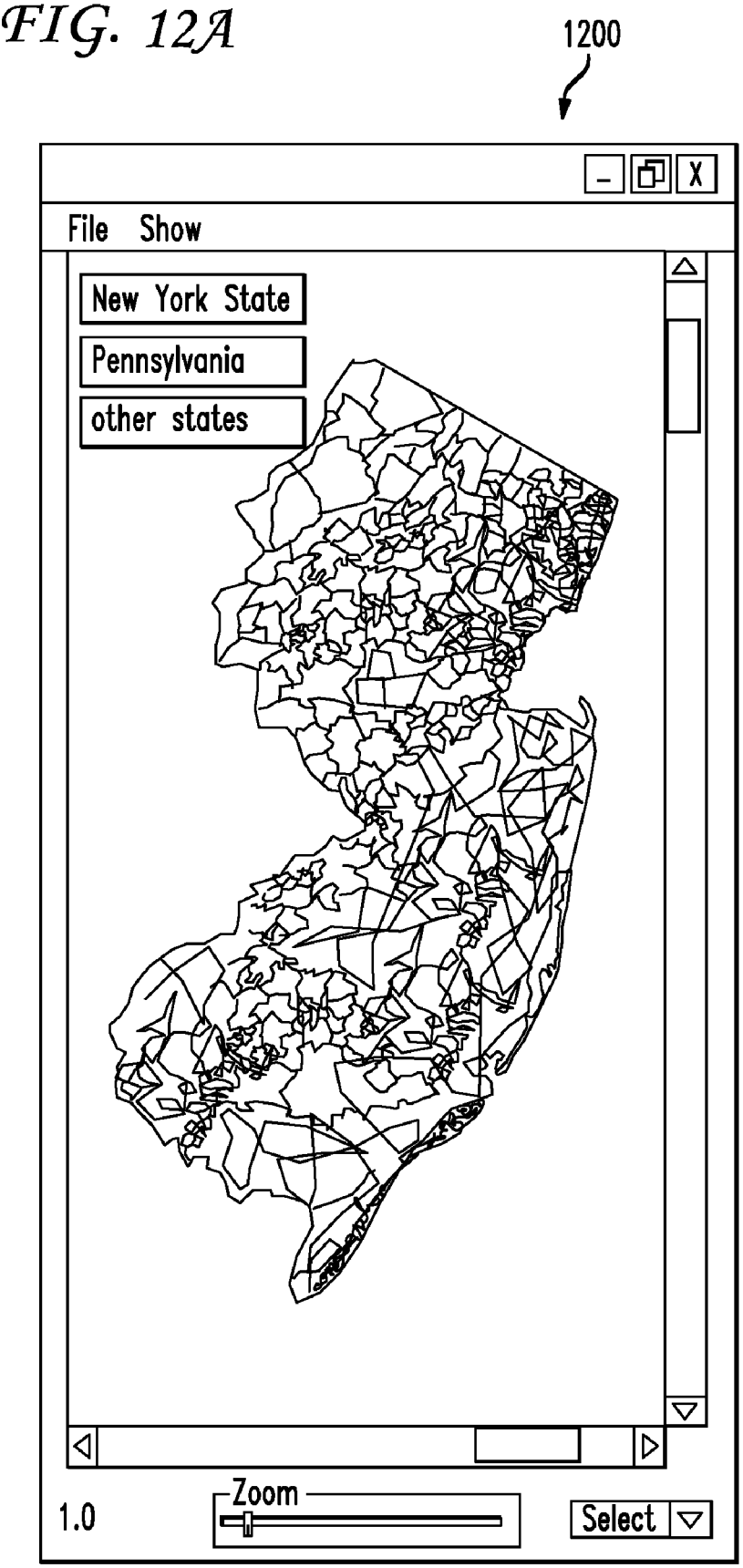
FIG. 12A illustrates a geographic view of hospital admissions in a window.
Figure 12B:
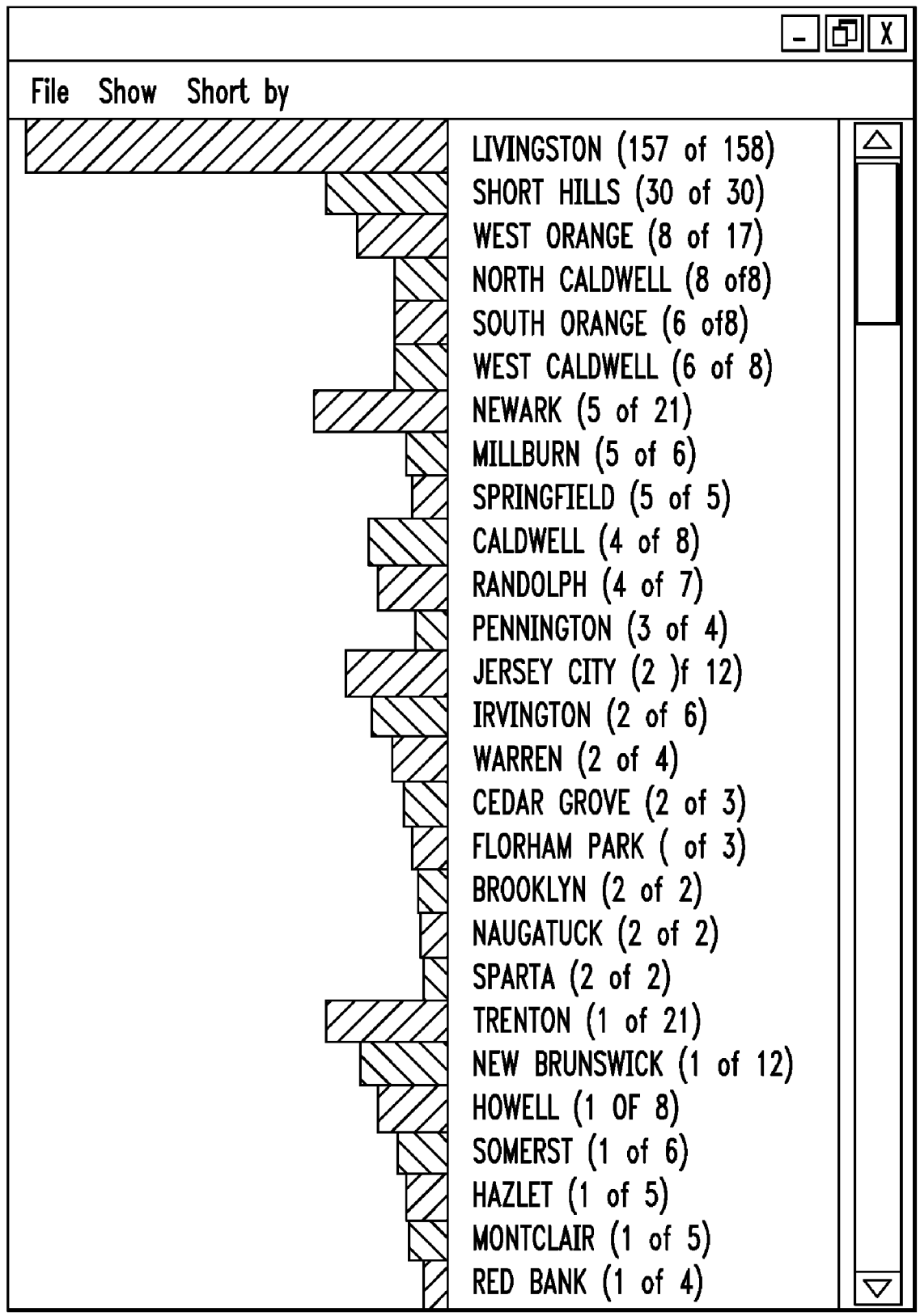
FIG. 12B illustrates a listing of where patients live who visited a hospital shown in window.

FIGS. 12A and 12B illustrate an example meningitis scare in New Jersey using the case manager. Window 1200 includes various counties or other geographic regions illustrating hospital emergency department admissions. Window 1202 in FIG. 12B illustrates a comparison of where the patients live that were admitted to the hospital. Presenting the information in this way enables the user to gain more information quickly to understand whether an alert should be issued.

Figure 13:
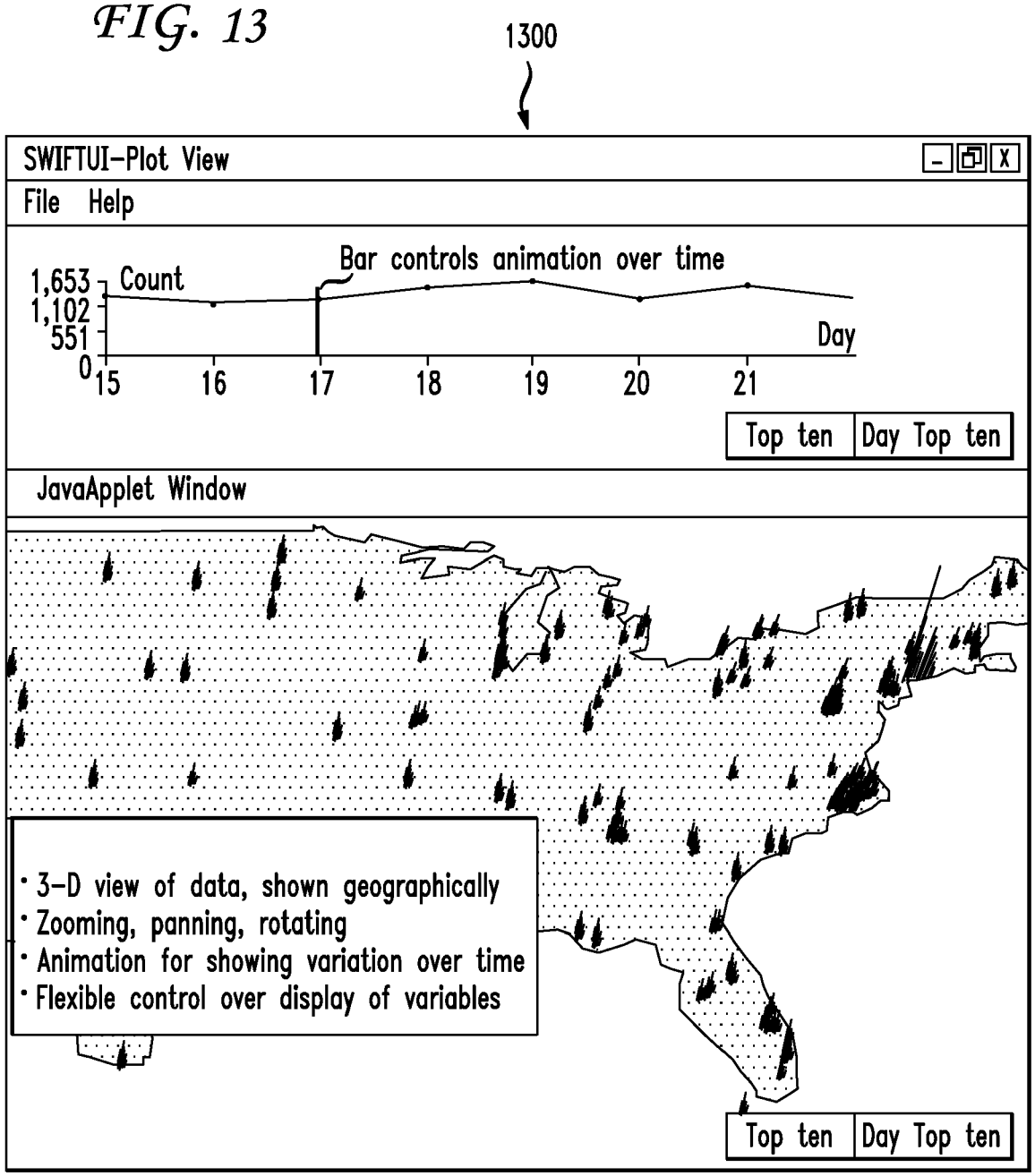
FIG. 13 illustrates an example user interface for animated time-series graphs.

Other user interfaces for example, may provide a graph which shows various states and then includes a three-dimensional perspective of areas where for example emergency department visits by patient home zip code, or positive blood tests by zip code of ordering location, include a height value which is related to a number of positives. Following common practice in statistical graphics, a graph may also include color variations to enable an expert to view the regions and identify selected cities or areas in which a blood test of a certain type has been found positive. FIG. 13 illustrates an example animated time-series graph. The top portion of window 1300 includes a daily count and the user can slide a bar which can control the animation over time, wherein as the user slides the bar the various geography based counts are modified so that trends may be visually viewed in three dimensions. The tool enables zooming, panning and rotating of data and animation for showing variation over time. Users have flexible control over the display of variables in this tool.

In a MDAP, there are various types of data which may be used to provide information. Primary data typically involves the raw data received from multiple domains or multiple sources. Secondary data relates to summaries of the primary data and tertiary data further relates to detected anomalies and scores based on threshold analyses of either primary or secondary data. Manually entered data may also be used. For example, there may be a mechanism for the user to enter data associated with the "Clinton effect" where the user has read the daily news and provides that data into the analysis.

FIG. 14 illustrates the various sets of objects which may be utilized in the upper layers 602, 604, and 606, of the early event detection funnel, FIG. 6; it also illustrates how various sets of objects may be utilized by MDAP. FIG. 14 illustrates data sources such as data source 1, 2 and 3, which may include primary, secondary or tertiary data. From these data sources, data extracts may be obtained, for example, the data extracts may be represented by a, b, c. Data extract a may come from source 1, data extract Kahlback-Leibler b may come from sources 2 and 3 and data extract c may come from data source 3. Next, FIG. 14 illustrates the application of various algorithms. These algorithms are shown as I, II, III, IV. For example, the MDAP may apply algorithms I and II to data extract a from source 1 or data algorithms I and III to data extract b and/or data algorithm IV to extract c. These anomaly detection algorithms typically generate an anomaly when a standardized score is produced by an algorithm specific to a particular time, place and data stream exceeds a threshold. It could be that no single score exceeds its threshold, but that a set of neighboring scores are close to the threshold. For example, the KFC and HWR algorithms do incorporate some logic for this, but the present invention provides a more general and powerful capability. Data may be extracted through means known to those of skill in the art, such as SQL, CYMBAL, PL/SQL series, which provide data extraction from a variety of different sources or multi various time series and arrays. Various intermediate data services may be used to build summaries or provide the next stage of information. Data may be extracted in a prepackaged or staging area and data summary tables may be available for rapid data extraction. Furthermore, message and/or architecture may be used to manage the implementation and processing of the various algorithms on the extracted data.

An aspect of the invention involves a rules engine which, in one implementation, is used by the MDAP to perform various analyses and produce the desired results. The rules engine may perform a number of functions such as anomaly detection, supporting anomaly algorithms from subject matter experts, a rules engine for smart thresholding, a separate rules engine for case creation, such as combining anomalies into cases, a rules engine for MDAP, for more complex case creation and refinement, a rules engine for case disposition and to support CEIM collaboration, and a rules engine to manage results for various stakeholders, analysts, and SME's.

Figure 15:
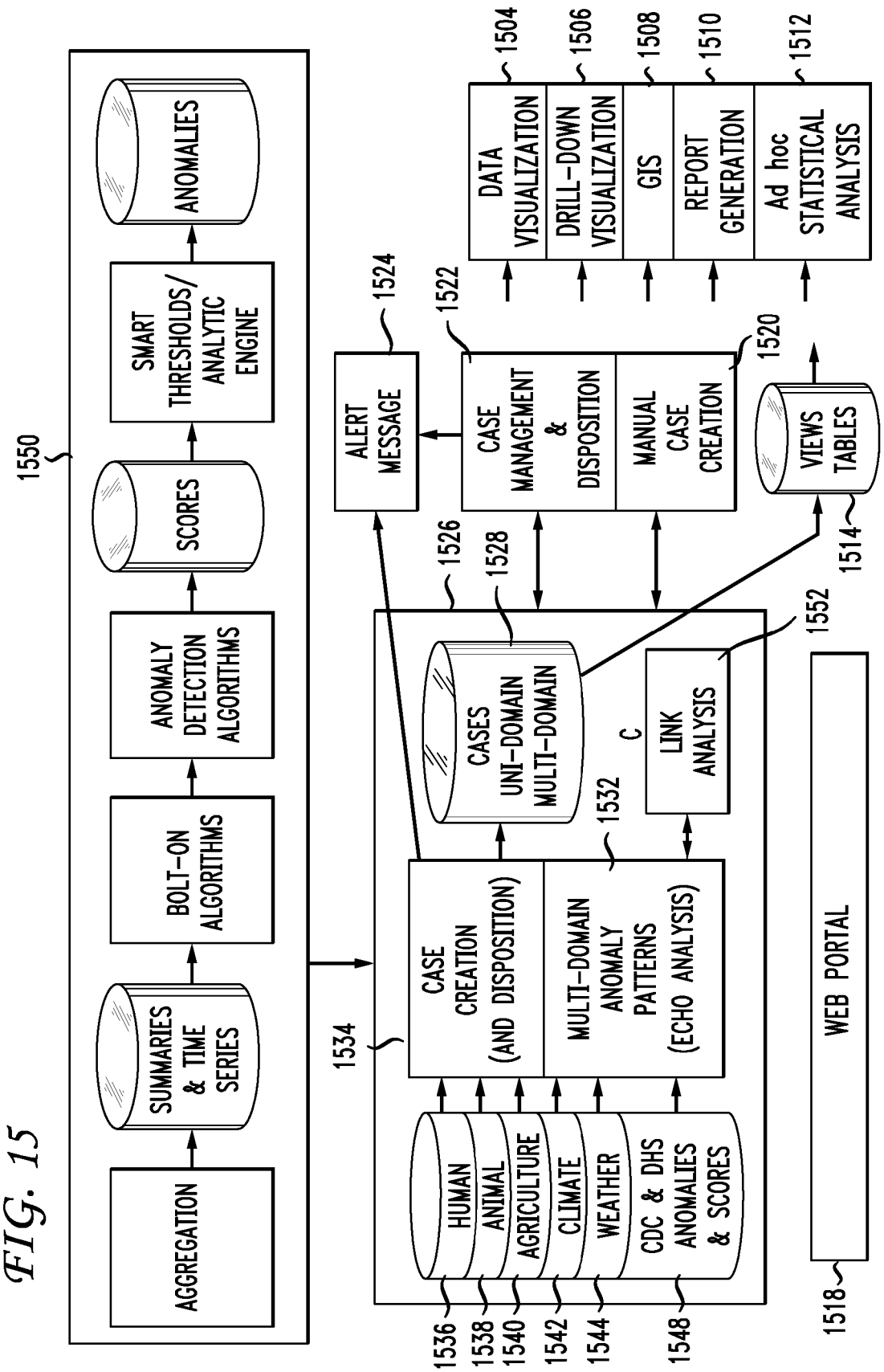
FIG. 15 illustrates a multi-domain case creation.

FIG. 15 illustrates the various components used in a multi-domain case creation scenario. The system 1550 illustrates the components leading up to a message alert. Features 1504 to 1512 include modules for data visualization 1504, drill down visualization 1506, GIF 1508, report generation 1510, and ad hoc statistical analysis 1512. There is a database of views and tables 1514 which communicates with a cases database 1528. A link analysis module 1552 communicates with a multi-domain anomaly pattern module 1532, as well as a case creation and disposition module 1534 which creates cases and stores them in the database 1528 for uni-domain and multi-domain databases. The term echo analysis describes the aspect of MDAP 1532 where an unusual pattern is echoed with smaller amplitude in neighboring regions, for example adjacent zip codes or related syndromes. The multiple domains are illustrated as providing human data 1536, animal data 1538, agricultural data 1540, climate data 1542, weather data 1544 and other departments that may have anomalies and scores 1548. As has been noted above, various components may go into the grouping of modules in 1526 which include aggregating data, summaries and time-series analysis of data, anomaly detection algorithms and bolt-on algorithms, each produce scores, much of them analyze very smart threshold and analytic engine to generate anomalies. These various components are shown in box 1550. A web portal 1518 may be used to enable a user to interact with the system. Modules 1526 also communicate with module 1520 for a manual case creation as well as a module 1522 which provides case management and disposition. The case management and disposition module 1522 and case creation and disposition modes 1534 may provide data to ultimately generate an alert message 1524.

As is shown in FIG. 16, an example method comprises a method of performing multi-domain surveillance. The method includes creating a database of normal patterns across multiple domains of domains of activity according to at least one region and based on time (1602), accessing data from the multiple domains to identify a plurality of anomalies from the normal pattern of activity (1604), receiving external input associated with at least one of the plurality of anomalies (1606), collecting the plurality of anomalies into a case for management, the case comprising a general container for anomalies, sub-threshold and super-threshold scores in a single or multiple domain (1608) and using collaborating evidence across multiple domains to adjust the likelihood that an event should be investigated (1610).

FIG. 17 illustrates another example method embodiment of the invention. As shown, a method of determining whether an event has occurred for further investigation may comprise calculating a score based on applying a selected algorithm from a plurality of algorithms to at least geographic data and human health related data (1702) or at least one other type of data. If the calculated score is above a threshold, the method comprises gathering further events associated with at least geographic data and the at least one other type of data (1704), summarizing potential anomalies from the gathered events using a probability algorithm (1706) and presenting a view based on geography associated with the at least one other type of data utilized in the calculation of the score (1708). As noted herein, the principles apply to any type of surveillance and are not limited to biosurveillance or healthcare issues.

There are several definitions used throughout the present application. For example, an event may be keyed by geography, data feeds, conditions, time and so forth. In the statistical anomaly detection setting, an event contains a score, the algorithm and the algorithm parameters. An anomaly may be defined as an event where the event score exceeds a preset threshold. For example, if the score is greater than or equal to the threshold (the value of which may be set according to geography, the data feed, other conditions, time, algorithm, or algorithmic parameters) then the event is an anomaly. A case as used herein is typically defined as a collection of events including anomalies. An alert is generally defined as a follow up action or typically a notification action which is generated from a case following expert review and in some circumstances automatically.

The knowledge base which may be used for any analysis of an MDAP may relate to thresholds which may be specific to geography, a data source, conditions, algorithms, date and so on. The knowledge base may also include history or logs of previous data or thresholds or anomalies. There may be case dossiers associated with case history management. There may be multi-domain anomaly patterns which may be used as part of the knowledge base to make decisions. Time may be involved such as a seasonal or holiday impacts. Other data such as the Dow industrial average may contribute to the knowledge base. Known algorithms associated with running quantities of data may be used in updating data. Signatures both real and electronic in some cases may be analyzed as well. The knowledge base may also provide for an adjustment of thresholds and may be used to modify the prioritization of cases.

The following paragraphs will describe the concept for the MDAP and how it addresses these preliminary areas of operation. It is presumed that as the MDAP matures, other uses will be envisioned that would improve the overall goal of early outbreak detection of emerging diseases. Additionally, the MDAP could be of value in other non-biosurveillance domains where anomaly detection efforts are required. For example, the US Coast Guards' Maritime Domain Awareness effort may benefit from a cross-domain view along with associated pattern matching requirements. The application of the MDAP in this as well as other future systems suggests that we define the architecture for the MDAP subsystem and develop its core capabilities.

A significant contribution of the MDAP is in the area of False Positive reduction. In order to provide a CEIM operation center with the lowest number of events to investigate, it is critical that cases are created that have the highest threat probability. A false positive can be defined as an anomaly, which is identified by the core anomaly detection engine (ADE) based on current thresholds and rules set in place by SME's, that turns out to be a non-event. The false positive could be an artifact of the data that appears to be a threat but upon further investigation turns out to be non-threatening. It is important that the surveillance system learn to identify and remove these false positive indications quickly so as to allow the investigators to concentrate on the real threats should they arise. Current fielded systems in biosurveillance have received criticisms due to the high number of false positives generated thereby rendering the system untenable. In the early stages of an a biosurveillance system deployed against newly acquired data streams where a substantial base-line of data norms has not been established, it would not be unreasonable to project thousands of false positive signals over a 24 hour period. To alleviate this overload of potential threats, one would be tempted to raise the detection threshold to a level that produced a reasonable number of events that could be researched in the allotted time. This regulating methodology has the potential of removing true signals (true positives) that could cause catastrophic results should a real threat be missed. Simply raising the detection threshold is not a viable option. Various approaches need to be put in place to filter out the false positives without removing the real threats. As stated, the MDAP provides an improved approach for a threatening event by looking for corroborating evidence in other data domains that either increase the probability of a threat, or more often, reduce the likelihood that the event is truly a threat needed to be investigated.

For example, let's assume that the data streams being analyzed include (1) numbers of patients presenting at a local hospital emergency department with symptoms of fever and cough, (2) percentages of child absenteeism at local schools and (3) volume of sales of analgesics and cough medicine at local pharmacies. Let's further assume that the ADE is set to generate single events to be investigated if the percentage of student absenteeism increases by 10% over a 24 hour period, or separately if the volume of sales of certain pharmaceuticals increases by 3% on any given day or separately again if the number of hospital ED visits increases by 10% over a 48 hour period. This scenario could generate two events (potential false positives) in each geographical zone (3000 zip codes or dozens of regions within the US) where the thresholds were exceeded and possibly one false negative or delayed event outlined below. By setting multi-domain rules across all three data streams and detection parameters that state when an increase in student absenteeism is followed by increased sales of cough medicine and analgesics within a suitable time delay followed by an increase in hospital emergency department visits also within a suitable time period (that could be <48 hours) an event is registered in the CEIM for investigation. As can be imagined, numerous events such as a local snow storm, flood or other environmental effects could cause the increase in absenteeism without the need for a biological investigation. Also, a market driven seasonal sale of certain pharmaceuticals could be the cause of the 3% increase that in actuality should not warrant a threat investigation. These events when viewed individually should not rise to the level of investigation (but did in this scenario). Only when combined and viewed in a Multi-Domain perspective are they meaningful.

Conversely, let's assume that the singular threshold for the number of visits to the hospital ED is set for an increase of 10% over a 48 hour period. During the buildup of this time period, no events would be generated as early outbreak indications. This scenario risks missing an outbreak in the early hours of development during which, if real, thousands of lives could have been saved. The MDAP system could be employed to create a rule that states should a 10% increase in the number of ED visits occur during a 48 hour period OR should ANY increase be detected in ED visits over a shorter time period that ALSO occurs with increases in absenteeism and pharmaceutical sales, generate an event.

One caveat needs to be noted with this scenario. As stated, the method employed in this MDAP example would use the Rules Engine to achieve the desired results. This method would work for sustained surveillance within a geographic region. It might not provide a solution as outlined for detecting similar or near-similar scenarios emerging in different regions across the US where the specific indicators and algorithm operating parameters (AOP's) may vary. Also, if the event was of an intended (i.e. terrorist) origin, SME's would want to create either manually or as auto-generated from the ADE scenarios-of-interest and store them within the MDAP data store that would, if found, generate an event in the CEIM. This is true Link-Analysis and Data Fusion that a mature biosurveillance system should provide.

The next use of the MDAP envisioned relates to event combination into the CEIM. An individual event from a single data domain may stand alone as a threat for investigation. However, this event may also be involved in a larger more comprehensive developing threat scenario. The scope of the larger threat may span other geospatial and temporal regions where all related events need to be viewed together for accurate situational awareness. These decisions would be under the control of the SME's as well as pre-established parameters set forth by default rules.

The next and perhaps most complex use of the MDAP would be to provide feedback to the ADE for enhanced performance along with recommendations for new algorithm use. Both manual feedback recommendations as well as automated feedback loops apply. Over time, the accuracy and improved performance of the ADE would partially be dependant on understanding what is the normal ebb-and-flow of arriving data, what settings within a specific data domain and geographical region are expected and what AOP settings are optimal.

Embodiments within the scope of the present invention may also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, flash card, or any other medium which can be used to carry or store desired program code means in the form of computer-executable instructions or data structures. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those of skill in the art will appreciate that other embodiments of the invention may be practiced in network computing environments with many types of computer system configurations, including personal computers, hand-held devices, multi-processor systems, microprocessor-based or programmable consumer electronics, network PCs, minicomputers, mainframe computers, and the like. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

Although the above description may contain specific details, they should not be construed as limiting the claims in any way. Other configurations of the described embodiments of the invention are part of the scope of this invention. Accordingly, the appended claims and their legal equivalents should only define the invention, rather than any specific examples given. The examples provided above relate primarily to biosurveillance and human health factors. However, the principles of the present invention may be further utilized to identify and process any kind of anomalies which may need the attention of a subject matter expert. For example, a company such as Walmart may utilize the principles of this invention to identify potential anomalies in their business value chain and their delivery mechanisms for products to various stores. In other words, the data that is used may be based on supply chain management such that anomalies may occur in which a particular product may need to be delivered to a particular location and the principles of the present invention may be utilized to identify that location and identify the product and improve the sufficiency in the timing of supply chain management.

We claim:

1. A method of performing multi-domain surveillance, the method comprising:
   analyzing, via a computer processor, first streamed data to identify healthcare transaction signatures in the first streamed data;
   based on the first streamed data, creating a database of signature patterns across multiple domains of biosurveillance activity according to at least one region and based on time;
   analyzing, via a computer processor, second streamed data to identify healthcare transaction signature anomalies in the second streamed data, wherein the signature anomalies are identified by comparing healthcare transaction data contained in the second streamed data to the signature patterns in the database to yield a comparison;
   accessing data in the database from the multiple domains to identify a plurality of anomalies based on the comparison of the signature patterns;
   collecting the plurality of anomalies into a case for management, the case comprising a general container for the plurality of anomalies, sub-threshold and super-threshold scores in one of a single domain and multiple domains; and
   using corroborating evidence across the multiple domains to adjust a likelihood that an event associated with the case should be investigated.

2. The method of claim 1, wherein the multiple domains comprise at least one of hospital data, school attendance data and medicare purchasing data.

3. The method of claim 1, further comprising:
   monitoring for possible current events while simultaneously monitoring a current roster of cases to determine whether to add a new event to the current roster of cases.

4. The method of claim 1, further comprising:
   receiving an input for supplementing the plurality of anomalies based on one or more anomalies across the multiple domains captured external to the processor.

5. A system for performing multi-domain surveillance, the system comprising:
- a processor;
- a first module configured to control the processor to analyze streamed data and identify healthcare transaction signatures in first streamed data;
- a second module configured to control the processor, based on the first streamed data, to create a database of signature patterns across multiple domains of biosurveillance activity according to at least one region and based on time;
- a third module configured to control the processor to analyze second streamed data to identify healthcare transaction signature anomalies in the second streamed data, wherein the signature anomalies are identified by comparing healthcare transaction data contained in the second streamed data to the signature patterns in the database to yield a comparison;
- a fourth module configured to control the processor to access data in the database from the multiple domains to identify a plurality of anomalies from the signature patterns;
- a fifth module configured to control the processor to collect the plurality of anomalies into a case for management, the case comprising a general container for the plurality of anomalies, sub-threshold and super-threshold scores in one of a single domain or multiple domains; and
- a sixth module configured to control the processor to use corroborating evidence across the multiple domains to adjust a likelihood that an event associated with the case should be investigated.

6. The system of claim 5, wherein the multiple domains comprise at least one of hospital data, school attendance data and medicare purchasing data.

7. The system of claim 5, further comprising:
- a seventh module configured to control the processor to monitor for possible current events while simultaneously monitoring a current roster of cases to determine whether to add a new event to the current roster of cases.

* * * * *